United States Patent [19]

Hargis

[11] Patent Number: 4,798,894

[45] Date of Patent: Jan. 17, 1989

[54] GEM CYCLODIALKYLATION OF AMINES AND AMIDES

[75] Inventor: Duane C. Hargis, Baton Rouge, La.

[73] Assignee: Ethyl Corporation, Richmond, Va.

[21] Appl. No.: 48,585

[22] Filed: May 11, 1987

[51] Int. Cl.[4] .................. C07D 473/34; C07D 295/02
[52] U.S. Cl. ........................ 544/277; 544/330; 544/331; 544/336; 544/405; 546/105; 546/184; 546/192; 546/193; 546/203; 546/240; 546/245; 546/251; 546/260; 546/281; 546/314; 546/344; 546/346; 548/400; 548/529; 548/540; 548/560; 548/562; 548/564; 548/574; 548/577; 548/578; 548/579
[58] Field of Search ............... 546/105, 184, 192, 193, 546/203, 240, 245, 251, 260, 281, 314, 344, 346; 544/277, 330, 331, 336, 405; 548/400, 529, 540, 560, 562, 564, 574, 579, 578

[56] References Cited

U.S. PATENT DOCUMENTS

| | | | |
|---|---|---|---|
| 2,012,801 | 8/1935 | Andrussow et al. | 564/305 |
| 3,086,017 | 4/1963 | Denton | 544/106 |
| 3,729,475 | 4/1973 | Williamson et al. | 546/233 |
| 3,830,923 | 8/1974 | Williamson et al. | 514/331 |
| 3,853,887 | 12/1974 | Pinke et al. | 546/191 |
| 3,868,420 | 2/1975 | Evans et al. | 564/409 |
| 3,900,479 | 8/1975 | Massie | 546/191 |
| 3,968,079 | 7/1976 | Pinke et al. | 524/102 |
| 3,975,400 | 8/1976 | Himmele | 548/554 |
| 3,977,987 | 8/1976 | Pinke et al. | 252/50 |
| 3,991,203 | 11/1976 | Rajadhyaksha | 514/24 |
| 4,077,919 | 3/1978 | Schulze | 521/129 |
| 4,418,005 | 11/1983 | Dodd et al. | 502/217 |
| 4,605,766 | 8/1986 | Hargis | 564/409 |
| 4,626,592 | 12/1986 | Hargis | 546/192 |

FOREIGN PATENT DOCUMENTS

| | | | |
|---|---|---|---|
| 0148009 | 10/1985 | European Pat. Off. | 564/409 |
| 768142 | 7/1934 | France | 564/305 |
| 851178 | 1/1940 | France | 548/579 |
| 7400259 | 1/1974 | Japan | 548/543 |
| 809752 | 3/1959 | United Kingdom | 564/395 |
| 1247594 | 9/1971 | United Kingdom | 546/251 |

OTHER PUBLICATIONS

*Chemical Abstracts*, vol. 36, Abstract No. 19157[2] (1942).
Bourns, Embleton, and Hansuld, *Canadian Journal of Chemistry*, vol. 30, pp. 1–8 (1952).
Hatada, Shimada, Ono, and Keii, *Journal of Catalysis* 37, pp. 166–173 (1975).
Ono, Hatada, Fujita, Halgeri, and Keii, *Journal of Catalysis* 41, pp. 322–328 (1976).
Hatada and Ono, *Bulletin of the Chemical Society of Japan*, vol. 50 (10), pp. 2517–2521 (1977).
Hatada, Fujita, and Ono, *Bulletin of the Chemical Society of Japan*, vol. 51 (8); 2419–2420 (1978).
Bourns, Embleton, Hansuld, *Organic Syntheses*, vol. 34, pp. 79–82.
*Chemical Abstracts*, vol. 44, 1092a (1950).
*Chemical Abstracts*, vol. 45, 1627e (1951).
*Chemical Abstracts*, vol. 45, 5680b (1951).
*Chemical Abstracts*, vol. 46, 964d (1952).
*Chemical Abstracts*, vol. 46, 7125f (1952).
*Chemical Abstracts*, vol. 47, 124b (1953).
*Chemical Abstracts*, vol. 47, 3351h (1953).
*Chemical Abstracts*, vol. 48, 739g (1954).
*Chemical Abstracts*, vol. 48, 2783a (1954).

(List continued on next page.)

*Primary Examiner*—Richard A. Schwartz
*Attorney, Agent, or Firm*—John F. Sieberth

[57] ABSTRACT

Compounds containing at least one N,N-dialkylatable amino or amido group (e.g., aniline, dodecylamine, acetamide) are converted in a highly efficient manner into gem cyclodialkylated compounds by reaction with an unstrained cyclic ether (e.g., tetrahydrofuran) or a polyol (e.g., 1,4-butane diol) cyclizable to an unstrained ether using titanium dioxide catalysts that have prior to use:

(1) a surface area of at least 70 square meters per gram (as determined by the BET method), and
(2) the capability of chemically adsorbing at 100° C. at least $35 \times 10^4$ millimoles of gaseous ammonia per square meter of surface area.

20 Claims, 2 Drawing Sheets

OTHER PUBLICATIONS

*Chemical Abstracts*, vol. 49, 6225c (1955).
*Chemical Abstracts*, vol. 50, 304h (1956).
*Chemical Abstracts*, vol. 50, 3393e (1956).
*Chemical Abstracts*, vol. 50, 7100g (1956).
*Chemical Abstracts*, vol. 52, 354i (1958).
*Chemical Abstracts*, vol. 52, 355b (1958).
*Chemical Abstracts*, vol. 53, 15040f (1959).
*Chemical Abstracts*, vol. 54, 3363d (1960).
*Chemical Abstracts*, vol. 55, 11335d (1961).
*Chemical Abstracts*, vol. 64, 14121f (1966).
*Chemical Abstracts*, vol. 66, 85703s (1967).
*Chemical Abstracts*, vol. 70, 68133w (1969).
*Chemical Abstracts*, vol. 73, 3802f (1970).
*Chemical Abstracts*, vol. 75, 20202u (1971).
*Chemical Abstracts*, vol. 77, 126023t (1972).
*Chemical Abstracts*, vol. 78, 111114v (1973).
*Chemical Abstracts*, vol. 78, 71927d (1973).
*Chemical Abstracts*, vol. 81, 3759n (1974).
*Chemical Abstracts*, vol. 81, 105160c (1974).
*Chemical Abstracts*, vol. 82, 129947a (1975).
*Chemical Abstracts*, vol. 83, 114198q (1975).
*Chemical Abstracts*, vol. 86, 139030d (1977).
*Chemical Abstracts*, vol. 88, 120895j (1978).
*Chemical Abstracts*, vol. 89, 108914c (1978).
*Chemical Abstracts*, vol. 91, 211183d (1979).
*Chemical Abstracts*, vol. 93, 150116b (1980).

GEM CYCLODIALKYLATION OF AMINES AND AMIDES

TECHNICAL FIELD

This invention relates to an enhanced catalytic process for the N,N-cyclodialkylation of amino and/or amido groups.

BACKGROUND

In my U.S. Pat. No. 4,626,592, issued Dec. 2, 1986, and in my reissue application Ser. No. 029,455, filed Mar. 23, 1987, I have shown, inter alia, that amines and amides are N,N-cyclodialkylated by reaction with an unstrained cyclic ether in the presence of a B subgroup metal oxide alkylation catalyst preferably a Group IV-B metal oxide such as titanium dioxide.

In French Pat. No. 851,178, published Jan. 4, 1940, it is indicated that N-alkyl-, N-cycloalkyl-, N-aralkyl-, and N-arylpyrrolidines are obtained by subjecting tetrahydrofuran and primary alkyl-, cycloalkyl-, aryalkyl-, or aryl amines at a high temperature to the action of dehydrating catalysts such as alumina, bauxite, the oxides of thorium, titanium and zirconium, the phosphates and borates of aluminum, zinc, cadmium, tin or silver, and silica gel. See also the abstract of this patent appearing in *Chemical Abstracts*, Vol. 36, Abstract 1957$^2$ (1942). Over the years, alumina has generally been regarded as the most efficacious catalyst for gem cyclodialkylation reactions of this type.

THE INVENTION

It has now been discovered that titanium dioxide having certain surface characteristics and surface acidity properties are unusually effective as catalysts in gem cyclodialkylation reactions. In fact, significant improvements in activity and selectivity are achievable by the practice of this invention as compared to the best results given in the literature involving use of alumina as the catalyst.

Thus in accordance with one embodiment of this invention, there is provided a process of converting an N,N-dialkylatable amino or amido group into an N,N-cyclodialkylated amino or amido group which comprises reacting a compound containing at least one N,N-dialkylatable amino or amido group with (a) an unstrained cyclic ether co-reactive therewith or (b) a polyol cyclizable to an unstrained cyclic ether co-reactive therewith in the presence of a viable titanium dioxide alkylation catalyst characterized by having prior to use a surface area of at least 70 square meters per gram as determined by the BET method and by having prior to use the capability of chemically adsorbing at 100° C. at least $35 \times 10^{-4}$ millimoles of gaseous ammonia per square meter of surface area, so that at least one such N,N-dialkylatable amino or amido group is transformed into a N,N-cyclodialkylated amino or amido group, respectively. Preferably the titanium dioxide of the catalyst is in the anatase crystalline form. Most preferably it has the capability prior to use of chemically adsorbing at 100° C. at least $40 \times 10^{-4}$ millimoles of gaseous ammonia per square meter of surface area.

The process of this invention is preferably conducted in the vapor phase by contacting a vapor phase mixture of the reactants with a bed of the catalyst. However, the reaction may also by conducted in other ways, for example it may be performed in the liquid phase in the presence of the particular types of titanium dioxide catalysts referred to above.

These and other embodiments and features of this invention will be still further apparent from the ensuing description, appended claims and the accompanying drawing which graphically illustrates the results achievable by the practice of this invention.

DETAILED DESCRIPTION OF THE INVENTION

Figure 1:
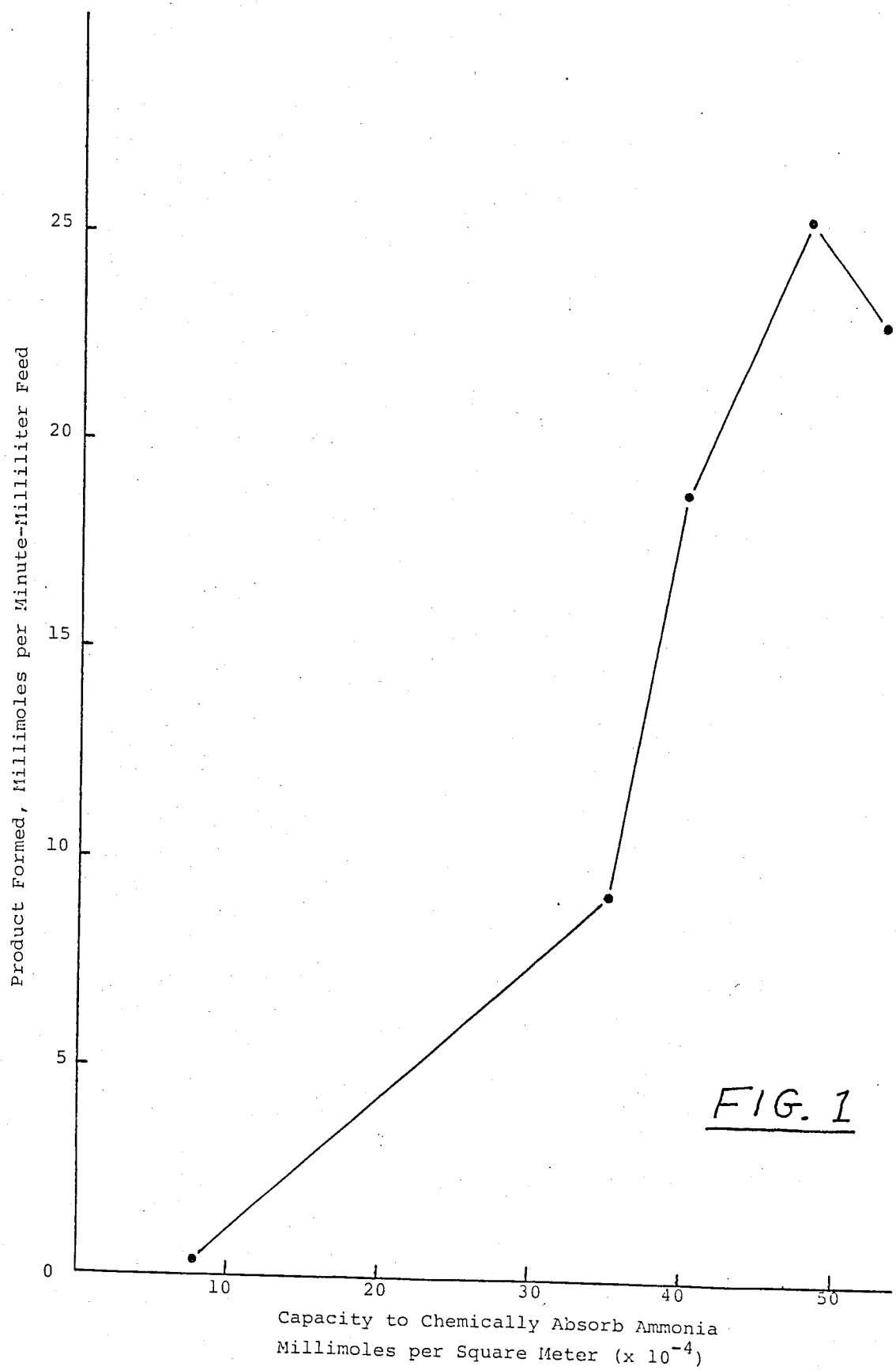
FIG. 1 is a plot of experimental results obtained with titanium dioxide catalysts having different surface areas and capacities for chemically adsorbing ammonia at 100° C.

As noted above, the titanium dioxide utilized as the catalyst in the practice of this invention has particular surface characteristics—i.e., it has an initial surface area of at least 70 square meters per gram as determined by the BET method and it has prior to use the capability of chemically adsorbing at 100° C. at least $35 \times 10^{-4}$ millimoles, and preferably at least $40 \times 10^{-4}$ millimoles of gaseous ammonia per square meter of surface area. As is well known in the art, the "BET" method of surface area determination represents the method developed and published by Brunauer, Emmett and Teller. See for example *J. Am. Chem. Soc.*, 1938, Vol. 60, pages 309 et seq.

The surface acidity characteristics of the titanium dioxide catalyst used pursuant to this invention are readily determined by exposing a sample of the catalyst to ammonia gas at at 100° C. and determining the number of millimoles of ammonia that are chemically adsorbed (i.e., chemically bound) per gram of the catalyst. This in turn enables calculation of the number of millimoles of ammonia adsorbed per square meter of surface area as determined by the BET method. As will be shown hereinafter, titanium dioxide catalysts possessing these characteristics have been found by actual test to give exceptionally good results in the gem cyclodialkylation reaction—substantially better than titanium dioxide catalysts which do not possess these characteristics. Moreover the results achieved in the practice of this invention were found to be superior to the best results reported in the literature for gem cyclodialkylation reaction in which alumunia catalysts were used. Thus surprisingly, this invention surpasses in effectiveness the alumina catalysts which have heretofore been regarded as the most effective for this use.

In measuring the amount of ammonia that can be adsorbed by a given source or grade of titanium dioxide it is necessary to take into account the fact that titanium dioxides that have surface areas of 70 square meters per gram and above are capable of adsorbing ammonia both by chemical adsorption and by physical adsorption. The former involves actual chemical bonding to the surface whereas the latter merely involves physical retention of ammonia on the surfaces of the titanium dioxide. Thus to distinguish between the amount of ammonia chemically adsorbed and the amount of ammonia physically adsorbed by a given titanium dioxide sample, two measurements are made under controlled conditions. The first involves measuring the total amount of ammonia that is adsorbed at 100° C. on a known quantity of titanium dioxide of known surface area (the surface area having been determined by the BET method). This represents the total of both chemical and physical adsorption. Then this same sample of titanium dioxide is subjected to vacuum conditions while maintained at the constant 100° C. temperature so that the physically adsorbed ammonia is purged from the sample. As a consequence of this vacuum treatment, only the chemically bound ammonia is retained by the sample. Then the sample is again exposed to ammonia at 100° C. and a second measurement is made of the amount of ammonia that is taken up by the sample. In this case the titanium dioxide sample is only able to take up ammonia by physical adsorption on the surface—its ability to chemically bind ammonia having been satiated in the first exposure to ammonia. Thus the volume of ammonia in this second instance is smaller than that taken up in the first instance and the difference therebetween represents the volume of ammonia chemically adsorbed by the titanium dioxide. Since the conditions of temperature and pressure are known it is therefore possible to calculate the number of millimoles of ammonia chemically adsorbed by titanium dioxide sample at 100° C. which in turn is readily converted into the number of millimoles of ammonia chemically adsorbed per square meter of surface area since the number of square meters per gram in the titanium dioxide sample is known from the BET determination.

Figure 2:
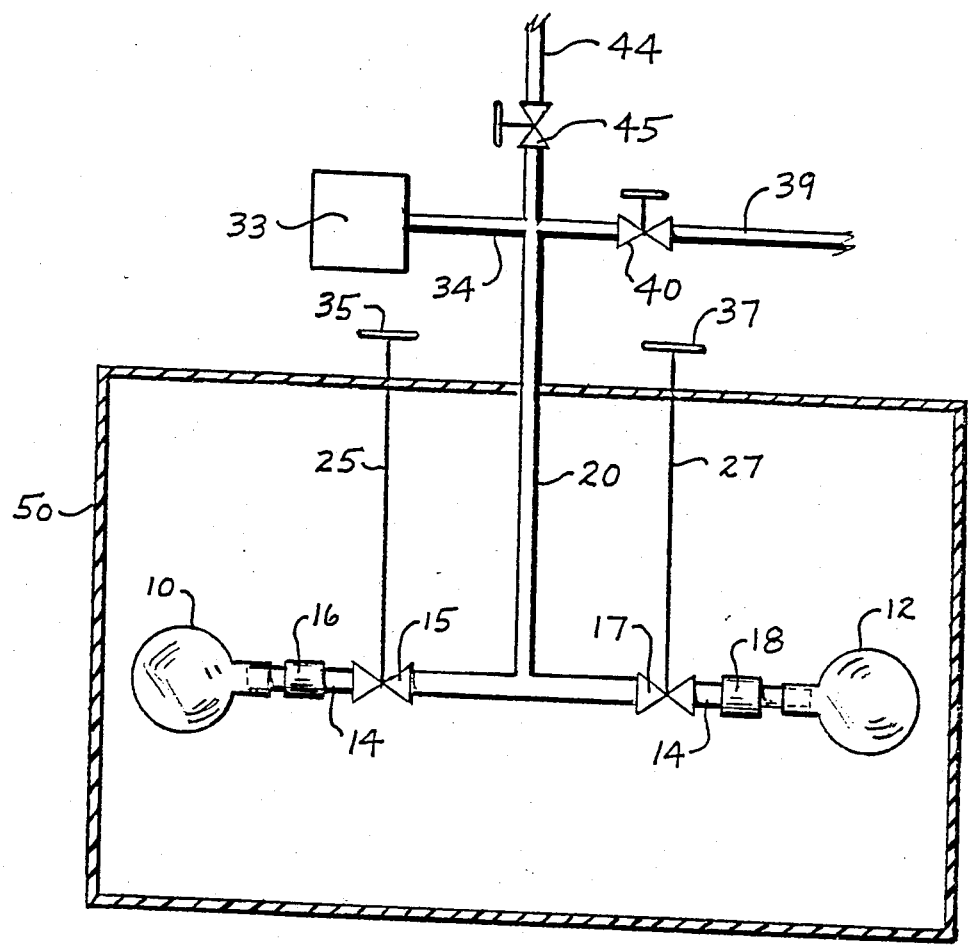
FIG. 2 is a section view (partly schematic and not to scale) of a typical apparatus useful for determining the capacity of titanium dioxide samples to chemically adsorb ammonia at 100° C.
Figure 3:
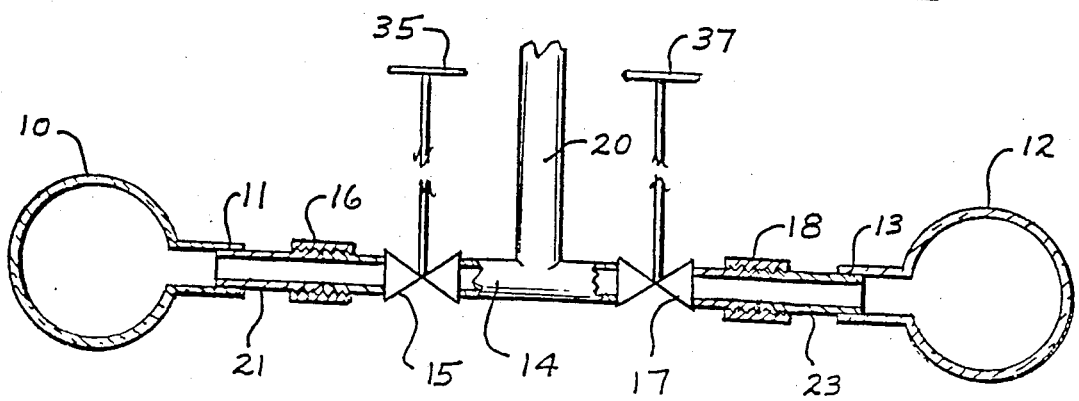
FIG. 3 is an enlarged section view (partly schematic and not to scale) of a portion of the apparatus of FIG. 2.

While various types of apparatus and procedures may be used to determine the amount of ammonia that can be chemically adsorbed by a given source or grade of titanium dioxide, apparatus such as depicted in FIGS. 2 and 3 has be found convenient and suitable for this purpose. Referring to FIGS. 2 and 3 (which are partly schematic and not to scale), oven 50 houses a pair of glass bulbs, 10,12 of known, calibrated volumes. Each bulb is sealed onto a metal tube 21,23 having a thermal expansion essentially equal to that of the glass (e.g., Pyrex glass and Kovar metal alloy) at 11 and 13, respectively. Each such bulb unit is detachably attachable to the opposite ends of a stainless steel tube or line 14 by means of a suitable gas and vacuum tight fitting 16,18, such as a Swagelok fitting, a Gyrolok fitting, or the like. Valves 15 and 17 are positioned in line 14 so as to enable either or both of bulbs 10 and 12 to be placed in open communication with line 14 or sealed off therefrom. Line 14 is intercepted at its middle portion by a vertically positioned stainless steel line 20. Since valves 15 and 17, line 14 and most of line 20 are encased within oven 50, valves 15 and 17 are equipped with suitably elongated stems 25 and 27 respectively so that these valves may be operated by handles 35 and 37 which are disposed to the exterior of the oven. The upper portion of line 20 is branched by means of line 39 leading to a source (not shown) of gaseous ammonia and line 34 leading to manometer 33, preferably a digital manometer such as a Datametric manometer, for measuring the pressure within the system. The upper end of line 20 can be sealed off or placed in direct communication with line 44 by means of valve 45. Line 44 communicates directly to a vacuum pump or other vacuum system (not shown). Valve 40 in line 39 enables ammonia to be admitted to or sealed off from the system as desired. Thus the entire system is leakproof and the system can be exposed either to ammonia gas or to a vacuum by appropriate manipulation of the valves.

In using the system depicted in FIG. 2, the following procedure is used:

1. A weighed sample of titanium dioxide is placed in bulb 10 which is then attached to the system by means of fitting 16.

2. With the entire system assembled (as depicted), with the temperature in oven 50 held constant at 100° C., and with valves 15, 17 and 45 open and valve 40 closed, the entire system is evacuated by means of the vacuum pump, preferably to a pressure of less than 0.01 mm of mercury.

3. Valves 15 and 45 are closed.

4. Valve 40 is opened so that ammonia is admitted to bulb 12 to a predetermined, known pressure.

5. Valves 17 and 40 are then closed. At this point it is possible to calculate the molar quantity of ammonia in bulb 12 by means of the well known gas laws, since the pressure, volume and temperature of the contents of bulb 12 are known. In this connection, it will be understood that the volume of bulb 12 includes the volume of metal tube 23 and the volume of that portion of line 14 extending between its outer end and valve 17. The same considerations apply as regards the known volume of bulb 10.

6. Lines 14 and 20 are evacuated by opening valve 45 so that these lines are purged by means of the vacuum pump.

7. Valve 45 is closed and valve 15 is opened.

8. Valve 17 is opened so that ammonia passes from bulb 12 into bulb 10 containing the titanium dioxide sample.

9. After a period of one hour, the pressure in the system is noted from manometer 33 and the following calculations are made: (a) the total quantity of ammonia adsorbed by the titanium dioxide sample, (b) the molar quantity of ammonia remaining in bulbs 10 and 12 and within the rest of the system extending to closed valves 40 and 45, and (c) the total quantity of ammonia that has left from bulb 12.

10. Valve 17 is closed and the system is evacuated by opening valve 45 to the action of the vacuum pump.

11. After the evacuation has been completed, valves 15 and 45 are closed and valves 17 and 40 are opened to recharge bulb 12 with ammonia. Valves 17 and 40 are then closed and valve 45 is opened to evacuate the system (except for bulbs 10 and 12). Valve 45 is then closed.

12. Valves 15 and 17 are opened and the procedure of step 9 above is repeated. In this instance the amount of ammonia adsorbed by the titanium dioxide sample results only from surface adsorption (physical adsorption as distinguished from chemical adsorption). The difference in the quantities of ammonia adsorbed by the titanium dioxide in steps 9 and 12 represents the amount of ammonia chemically adsorbed by the titanium dioxide subjected to this procedure.

The practice and advantages of this invention were demonstrated by means of a series of experiments in which various types of titanium dioxide catalysts were employed in the reaction between tetrahydrofuran and dodecylamine. All runs were made in a 1" inside diameter stainless steel, packed bed, flow-through reactor, 19" in length, fitted at the top with a helium flush line and a liquid feed line. The catalyst bed was supported by five millimeter glass beads positioned in the base of the reactor. Glass beads were also placed on top of the catalyst bed to ensure complete vaporization of the liquid feed prior to contact of the catalyst bed. Temperature within the reactor was measured by thermocouples in a thermocouple well passing through the catalyst bed. The premixed feed from a buret reservoir was fed to the top of the reactor by means of a calibrated Milton Roy Mini-Pump. Liquid product was collected in a wet ice trap. The volume of effluent gas was measured with a wet test meter. All reactions were performed at a temperature of 300° C. In each case the reactants (tetrahydrofuran and dodecylamine) were fed in a 2:1 molar ratio, respectively.

Four different titanium dioxide catalysts were employed in these experiments. All were obtained from commercial sources and are identified as follows:

Catalyst A—Harshaw—Ti-XL-388A-4-1-2
Catalyst B—Harshaw—Ti-0720-T 1/8
Catalyst C—Harshaw—Ti-X-649-84-1
Catalyst D—Stauffer—E-8457.1-RS Each of these catalysts was calcined in air at 300° C. for 3.5 hours. Each was in the anatase crystalline form. A separate portion of Catalyst D was calcined at 450° C. for 3.5 hours and this catalyst is designated hereinafter as Catalyst E. In each experiment, the volume of the catalyst was 20 cubic centimeters. Surface areas of the catalysts were determined by the standard BET method. The crystalline phase was determined by X-ray diffraction. Surface acidity was determined by measuring adsorption of ammonia gas at 100° C. in the manner described above. The results from this series of experiments are shown in the following table:

TABLE

| Catalyst | A | B | C | D | E |
|---|---|---|---|---|---|
| Calcine Temperature, °C. | 300 | 300 | 300 | 300 | 450 |
| Catalyst Weight, g | 17.9 | 17.3 | 4.42 | 13.1 | 14.6 |
| Surface Area, m$^2$/g | 58.1 | 72.7 | 89.4 | 136.5 | 94.4 |
| Total Surface Area, m$^2$ | 1040 | 1258 | 395 | 1788 | 1378 |
| Amt NH$_3$ Chemically Adsorbed, mmoles/g | .045 | .295 | .317 | .664 | .507 |
| Amt NH$_3$ Chemically Adsorbed, mmoles | .80 | 5.1 | 1.4 | 8.7 | 7.4 |
| Amt NH$_3$ Chemically Adsorbed, mmoles/m$^2$ ($\times 10^{-4}$) | 7.7 | 40.5 | 35.4 | 48.7 | 53.7 |
| Amine Conversion, wt % | 1.2 | 56.9 | 23.9 | 66.6 | 62.9 |
| Product Selectivity, wt % | 82 | 83 | 90 | 90 | 88 |
| Product Formed, mmoles/min-ml feed | .41 | 18.8 | 9.1 | 25.5 | 23.0 |

It will be noted from the above tabulated data that catalyst activity was expressed as millimoles of product formed per minute per unit of feed rate. In this way small variations in feed rate were eliminated.

FIG. 1 presents a plot of the data from the above five runs in which the ordinate is millimoles of product formed per minute per unit of feed rate and the abscissa is millimoles of ammonia chemically adsorbed per square meter of catalyst (x $10^{-4}$). Thus the higher the value on the ordinate the more effective was the catalyst. It is readily apparent from the FIGURE that the titanium dioxide catalysts which met the surface area and ammonia adsorption criteria of this invention were exceptionally effective in the gem cyclodialkylation reaction. Further it can be seen that a very sharp increase in performance took place when going from a catalyst having a chemical absorptive capacity of about $35 \times 10^{-4}$ to about $40 \times 10^{-4}$ millimoles of gaseous ammonia per square meter of surface area. On the other hand titanium dioxide catalysts not meeting the surface area and ammonia adsorption criteria of this invention, although operative, are substantially less effective.

It is interesting to compare the results achievable by the practice of this invention with those obtained with alumina as recently reported by R. E. Walkup and S. Searles, Jr., *Tetrahedron*, 1985, Volume 41, Number 1, pages 101 to 106. Although no rigorous experimental comparisons can be made, indications from available experimental data on the reaction between 2,6-diethylaniline and tetrahydrofuran are that product yields based on the reaction between 2,6-diethylaniline and tetrahydrofuran the amine and the tetrahydrofuran used in the process are substantially higher when using titanium dioxide catalysts pursuant to this invention.

The term "cyclodialkylation" is used herein in a generic sense to indicate that a cyclic group is formed on the nitrogen atom of the gem (i.e., N,N-)dialkylatable amino or amido group(s), which cyclic group may be saturated or unsaturated and may be composed solely of the nitrogen atom and carbon atoms or may contain one or more additional hetero atoms.

In the practice of this invention use is made of aliphatic, cycloaliphatic, aromatic, and heterocyclic compounds that contain at least one N,N-dialkylatable amino or amido group. The characteristics of the N,N-dialkylatable amino groups are the following:

(1) The amino groups are not so sterically hindered as to prevent the desired N,N-cyclodialkylation from occurring.

(2) The amino groups are substituted by at least one, and preferably by two, hydrogen atoms. When substituted by only one hydrogen atom, a second bond of the amino group is satisfied by a group, such as methyl, that can be displaced in the course of the N,N-cyclodialkylation reaction. In other words, the amino group has the formula

—NHR where R is hydrogen or a displaceable substituent such as an alkyl group or the like.

(3) The amino groups are bonded to organic groups or moieties that do not prevent the N,N-cyclodialkylation reaction from occurring.

The characteristics of the N,N-cyclodialkylatable amido groups are as follows:

(1) They have the formula

—CONH$_2$ (2) They are bonded to organic groups or moieties that do not prevent the N,N-cyclodialkylation reaction from occurring.

In short, this invention utilizes only amines and amides that undergo the desired cyclodialkylation reaction under the reaction conditions employed.

Typical aromatic amines usable as starting materials in my process include the single ring compounds such as aniline, o-toluidine, m-toluidine, p-toluidine, o-ethylaniline, m-ethylaniline, p-ethylaniline, o-isopropylaniline, m-isopropylaniline, p-isopropylaniline, 2,3-xylidine, 2,4-xylidine, 2,5-xylidine, 2,6-xylidine, 3,4-xylidine, 3,5-xylidine, 2,3-diethylaniline, 2,4-diethylaniline, 2,5-diethylaniline, 2,6-diethylaniline, 3,4-diethylaniline, 3,5-diethylaniline, 2,3-diisopropylaniline, 2,4-diisopropylaniline, 3,5-diisopropylaniline, 2,4-toluenediamine, 2,5-toluenediamine, 1,3-diaminobenzene, 1,3,5-triaminobenzene, and the like. Also usable are multiple ring compounds such as 4-aminobiphenyl, 1-naphthylamine, 2-naphthylamine, 1-anthrylamine, 1-phenanthrylamine, 1,4-diaminonaphthalene, 1,5-diaminonaphthalene, 4,4'-diaminobiphenyl, 4,4'-methylenebisaniline, and the like.

Suitably substituted aromatic amines may also be used, such as o-anisidine (2-aminoanisole), m-anisidine, p-anisidine, o-chloroaniline, m-chloroaniline, p-chloroaniline, anthranilonitrile (o-aminobenzonitrile or o-cyanoaniline), and the like.

Of the above described aromatic amines, the single ring aromatic amines are preferred. Aniline and ring alkylated anilines are the more preferred of the single ring aromatic amines. Most preferred are aniline, one or a mixture of two or more toluidine isomers or one or a mixture of two or more xylidine isomers.

In the N,N-cyclodialkylation process primary aromatic amines, such as those exemplified above, may be used. In addition, secondary aromatic amines may be used provided one of the substituents on the nitrogen atom is displaceable under the reaction conditions being used. Examples of such compounds include the N-alkylanilines, such as N-methylaniline, N-ethylaniline, N-methyl-p-chloroaniline, and various other similar compounds.

Moreover the N,N-cyclodialkylation process of this invention can be applied to aliphatic amines, such as methylamine, ethylamine, propylamine, butylamine, octylamine, dodecylamine, tetradecylamine, allylamine, benzylamine, 1-adamantanemethylamine (i.e., 1-aminomethyladamantane), ethanol amine, 2-chloroethylamine, etc.; cycloaliphatic amines such as cyclopropylamine, cyclobutylamine, cyclopentylamine, cyclohexylamine, cycloheptylamine, cyclooctylamine, cyclododecylamine, 1-adamantanamine, 1-aminoindan, etc.; and heterocyclic amines, such as 2-amino-pyridine, 3-aminopyridine, 4-aminopyridine, adenine, 2-amino-5-picoline, 2-amino-6-picoline, aminopyrazine, 2-aminopyrimidine, 9-amino-1,2,3,4-tetrahydroacridine, 2,6-diaminopyridine, 3,5-diaminopyridine, and the like.

Amides that can be used in the N,N-cyclodialkylation process of this invention are exemplified by formamide, acetamide, propionamide, and the like.

When conducting the N,N-cyclodialkylation reaction of this invention use is made of an unstrained cyclic ether that undergoes the N,N-cyclodialkylation reaction under the reaction conditions being used and with the amine or amide being used.

The characteristics of such ethers are as follows:

(1) They contain at least one oxygen atom in an at least five-membered ring system that is susceptible to ring opening under the reaction conditions employed.

(2) The ring system is free of ring components and ring substituents that prevent the N,N-cyclodialkylation reaction from occurring.

Among the cyclic ethers suitable for the practice of this invention are those which contain only carbon and an oxygen atom in an unstrained ring (i.e., the ring contains at least four carbon atoms and an oxygen atom bonded to two separate carbon atoms of the ring). Examples of such cyclic ethers include furan, pyran, the various dihydrofuran and dihydropyran isomers; tetrahydrofuran, tetrahydropyran, alkyl-substituted furans, dihydrofurans, tetrahydrofurans, dihydropyrans and tetrahydropyrans, such as 2-methyltetrahydrofuran, 3-methyltetrahydrofuran, 2,5-dimethyltetrahydrofuran, 2-methyltetrahydropyran, gamma-butyrolacetone; furfuryl alcohol; hydroxy and alkoxy-substituted furans, dihydrofurans, tetrahydrofurans, dihydropyrans and tetrahydropyrans, such as 2-methoxytetrahydrofuran, 3-hydroxytetrahydrofuran, 2-ethoxymethyl tetrahydrofuran, 2-butoxymethyl tetrahydrofuran; tetrahydro-2-furancarbinol, furfurylamine; 2-furaldehyde; tetrahydrofuroic acid, methyl tetrahydrofuroate, oxepane; and the like. Moreover, unstrained cyclic ethers having nitrogen in the ring such as 2-oxazolidone (which may also be considered a heterocyclic amine) can be used in the process. In the case of such cyclic ethers as tetrahydrofuran, tetrahydropyran and their suitably substituted congeners, reaction with primary aromatic amines such as aniline and nuclear alkylanilines (e.g., toluidine, xylidines, o-, m-, p-ethylaniline, 2,3-, 2,4-, 2,5-, 2,6-, 3,4-, and 3,5-diethylanilines, etc.) results in gem cyclodialkylation of the nitrogen atom with high conversions of the aromatic amine and very high product yields.

Instead of a cyclic ether reactant, use may be made of a suitable polyol, such as 1,4-butane diol, 2-butene-1,4-diol, 1,5-pentane diol, 1,4-pentane diol, 1,5-hexane diol, 2,3-dimethyl-1,4-butane diol, 3,7-octane diol, 1,6-hexane diol, 1,7-heptane diol, 2,5-hexane diol, 3-hexane-2,5-diol, diethylene glycol, 2,3-dibromo-2-butene-1,4-diol, and the like. Such polyols are characterized by having the hydroxyl groups separated by at least 4 carbon atoms. Thus, for example, reaction of 1,4-butane diol with an N,N-dialkylatable amine or amide forms essentially the same product as if tetrahydrofuran were used as the gem-cyclodialkylating agent. Indeed it is possible to employ in the process mixtures of suitable glycols and unstrained cyclic ethers such as tetrahydropyran and 1,5-pentane diol, and like mixtures. The reaction conditions and reactant ratios used when employing polyols are essentially the same as used for the cyclic ether reactants.

For the N,N-cyclodialkylation process of this invention, temperatures in the range of about 200° to about 350° C. are most preferred. While higher temperatures are feasible, the temperature used should take into consideration the thermal decomposition temperatures of the reactants and products as well as the effect of temperature on the activity of the particular heterogeneous titanium dioxide catalyst being employed.

The present invention is capable of being carried out in either a batch or continuous operation mode according to the available equipment and intentions of the operator. In addition, the various processes may be carried out either in the vapor phase or in the liquid phase, depending of course upon the reactants and temperature and pressure conditions in use. When conducted as a liquid phase process the reactants may be subjected to reaction either in bulk or in a suitable inert reaction solvent or diluent such as an inert hydrocarbon that exists in the liquid state under the reaction conditions being employed.

Although the process can be carried out in the liquid phase, it is preferable to conduct the process in the vapor phase using a fixed-bed or a moving or fluidized bed of the catalyst.

It is important when practicing this invention to use an active alkylation catalyst for the process. In this connection, the thermal history of the catalyst appears to be of importance to its activity. For example, exposure to temperatures as high as 450° C. and above may impair activity. Thus any given commercially available titanium dioxide catalyst may or may not be active in the process of this invention depending upon whether or not it was calcined and if so, whether the calcining temperature was high enough to destroy its catalytic activity for use in the process of this invention. Thus in selecting commercially available B-subgroup metal oxides for use in my process, one should attempt to secure materials that have not been calcined at excessively high temperatures that render them unsuitable in the present process. In cases where the manufacturers decline to supply such thermal history information, one should secure and test in the present process a variety of samples of candidate titanium dioxide catalysts otherwise meeting the surface parameters area and acidity given above and select one or more having the best or optimum activity for the particular reaction under consideration. In general, titanium dioxides having the anatase crystalline form have significantly higher catalytic activity than titanium dioxides having the rutile form.

The conditions used in the process of this invention are susceptible to considerable variation. For example, while my process is usually conducted with an excess of the cyclic ether reactant relative to the amine or amide reactant, a stoichiometric deficiency of the ether may be used. The ratio used will be influenced to some extent by the composition of the amine (i.e., whether it is a monoamine or a polyamine). In most cases the reaction mixture will contain about 0.5 to about 5 molar equivalents of the cyclic ether per molar equivalent of the amine or amide. In the case of reactions between cyclic monoethers and monoamines, the molar ratio of ether to amine is preferably in the range of about 1:1 to about 3:1.

It is possible to vary certain aspects and other features of the above described invention without departing from the lawful scope or true spirit thereof.

I claim:

1. The process of converting an N,N-dialkylatable amino or amido group into an N,N-cyclodialkylated amino or amido group which comprises reacting a compound containing at least one N,N-dialkylatable amino or amido group with (a) an unstrained cyclic ether co-reactive therewith or (b) a polyol cyclizable to an unstrained cyclic ether co-reactive therewith in the presence of a viable titanium dioxide alkylation catalyst characterized by having prior to use a surface area of at least 70 square meters per gram as determined by the BET method and by having prior to use the capability of chemically adsorbing at 100° C. at least $35 \times 10^{-4}$ millimoles of gaseous ammonia per square meter of surface area, so that at least one such N,N-dialkylatable amino or amido group is transformed into a N,N-cyclodialkylated amino or amido group, respectively.

2. A process of claim 1 wherein the ether has a single oxygen atom and at least four carbon atoms in the ring and said compound has at least one N,N-dialkylatable primary amino group in the molecule.

3. A process of claim 1 wherein said titanium dioxide is in the anatase crystalline form and before use has the capability of chemically adsorbing at 100° C. at least $40 \times 10^{-4}$ millimoles of gaseous ammonia per square meter of surface area.

4. A process of claim 1 wherein the reaction is conducted in the vapor phase by contacting a vapor phase mixture of the reactants with a bed of the catalyst.

5. A process of claim 1 wherein the reaction is conducted in the liquid phase in the presence of the catalyst.

6. A process of claim 1 wherein the reaction is conducted at a temperature of at least about 200° C. but below that at which the catalyst becomes inactive.

7. A process of claim 1 wherein said compound has at least one N,N-dialkylatable secondary amino group in the molecule.

8. A process of claim 1 wherein the reaction is conducted in the vapor phase by contacting a vapor phase mixture of the reactants with a bed of the catalyst and wherein the titanium dioxide is in the anatase crystalline form and before use has the capability of chemically adsorbing at 100° C. at least $40 \times 10^{-4}$ millimoles of gaseous ammonia per square meter of surface area.

9. The process of converting an N,N-dialkylatable amino group into an N,N-cyclodialkylated amino group which comprises reacting a compound containing at least one N,N-dialkylatable amino group with an unstrained cyclic ether co-reactive therewith in the presence of a viable titanium dioxide alkylation catalyst characterized by having prior to use a surface area of at least 70 square meters per gram as determined by the BET method and by having prior to use the capability of chemically adsorbing at 100° C. at least $35 \times 10^{-4}$ millimoles of gaseous ammonia per square meter of surface area, at a temperature of at least about 200° C. but below that at which the catalyst becomes inactive, so that at least one such N,N-dialkylatable amino group is transformed into an N,N-cyclodialkylated amino group.

10. A process of claim 9 wherein the ether has but a single ring composed of a furan ring system, a dihydrofuran ring system, a tetrahydrofuran ring system, a dihydropyran ring system or a tetrahydropyran ring system.

11. A process of claim 9 wherein said compound has at least one N,N-dialkylatable primary amino group in the molecule.

12. A process of claim 11 wherein said compound is a primary aromatic amine.

13. A process of claim 12 wherein the amine is a primary aromatic amine having one or two amino groups on one or two aromatic rings.

14. A process of claim 11 wherein said compound is a primary aliphatic amine.

15. A process of claim 14 wherein said amine is a monoalkyl amine.

16. A process of claim 9 wherein said titanium dioxide catalyst is in the anatase crystalline form and the reaction is conducted in the vapor phase by contacting a vapor phase mixture of the reactants with a bed of said catalyst.

17. A process of claim 9 wherein said compound is a primary aromatic amine or a primary aliphatic amine, wherein the reaction is conducted in the vapor phase by contacting a vapor phase mixture of the reactants with a bed of the catalyst and wherein the titanium dioxide is in the anatase crystalline form and before use has the capability of chemically adsorbing at 100° C. at least $40 \times 10^{-4}$ millimoles of gaseous ammonia per square meter of surface area.

18. A process for the production of N,N-cyclodialkylated amines which comprises reacting N,N-cyclodialkylatable primary or secondary aliphatic amine or N,N-cyclodialkylatable primary or secondary aromatic amine with an unstrained cyclic ether co-reactive therewith in the presence of a viable titanium dioxide alkylation catalyst characterized by having prior to use a surface area of at least 70 square meters per gram as determined by the BET method and by having prior to use the capability of chemically adsorbing at 100° C. at least $35 \times 10^{-4}$ millimoles of gaseous ammonia per square meter of surface area, at a temperature of at least about 200° C. but below that at which the catalyst becomes inactive, so that at least one such N,N-dialkylatable amino group is transformed into an N,N-cyclodialkylated amino group.

19. A process of claim 18 wherein the amine used in the reaction is a primary alkyl amine or a primary aromatic amine, wherein the ether has but a single ring composed of a furan ring system, a dihydrofuran ring system, a tetrahydrofuran ring system, a dihydropyran ring system or a tetrahydropyran ring system.

20. A process of claim 18 wherein the reaction is conducted in the vapor phase by contacting a vapor phase mixture of the reactants with a bed of the catalyst.

* * * * *